United States Patent
Weferling et al.

(10) Patent No.: US 6,329,544 B1
(45) Date of Patent: *Dec. 11, 2001

(54) PROCESS FOR PREPARING DIALKYLPHOSPHINIC ACIDS

(75) Inventors: Norbert Weferling, Hürth; Hans-Peter Schmitz, Brühl; Günter Kolbe, Kerpen, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/527,950

(22) Filed: Mar. 10, 2000

Related U.S. Application Data

(63) Continuation of application No. 09/198,541, filed on Nov. 24, 1998.

(30) Foreign Application Priority Data

Nov. 28, 1997  (DE) ............................................. 197 52 734
Nov. 10, 1998  (DE) ............................................. 198 51 618

(51) Int. Cl.$^7$ .................................................. C07F 9/30
(52) U.S. Cl. .................................................. 562/8; 524/133
(58) Field of Search ................................. 562/8; 524/133

(56) References Cited

U.S. PATENT DOCUMENTS

| | | | |
|---|---|---|---|
| 2,957,931 | 10/1960 | Hamilton et al. | 260/403 |
| 3,488,368 | 1/1970 | Spivack | 260/429.7 |
| 3,534,127 | 10/1970 | Spivack | 260/968 |
| 3,563,948 | 2/1971 | Spivack | 260/45.75 |
| 3,742,096 | 6/1973 | Spivack | 260/953 |
| 3,912,654 | 10/1975 | Heid et al. | 252/321 |
| 3,914,345 | 10/1975 | Kleiner et al. | 260/970 |
| 4,036,811 | 7/1977 | Noetzel et al. | 260/45.75 W |
| 4,208,322 | 6/1980 | Sandler | 260/45.75 K |
| 4,321,187 | 3/1982 | Granzow | 524/133 |
| 4,590,014 | 5/1986 | Wolf et al. | 260/502.4 R |
| 4,632,741 | 12/1986 | Wolf et al. | 204/157.73 |
| 4,939,285 | 7/1990 | Weis et al. | 558/214 |
| 4,972,011 | 11/1990 | Richardson et al. | 524/130 |
| 4,973,727 | 11/1990 | Gainer et al. | 558/133 |
| 5,780,534 | 7/1998 | Kleiner et al. | 524/133 |
| 6,207,736 | 3/2001 | Nass et al. | 524/126 |

FOREIGN PATENT DOCUMENTS

| | | |
|---|---|---|
| 0327496 | 8/1989 | (EP) . |
| 8505520 | 5/1984 | (ES) . |
| 1 558 606 A | 2/1969 | (FR) . |

OTHER PUBLICATIONS

E.E. Nifant'ev: "Acid catalysis in the hydrophosphorylation of olefins" Journal of General Chemistry USSR., vol. 50, No. 8/1,—Aug. 1980, pp. 1416–1423, XP002093427, New York US.

E.E. Nifant'ev: "Hydrophosphorylation of cyclopentenes" Journal of General Chemistry USSR., vol. 61, No. 1/1,—Jan. 1991 pp. 83–92, XP002093428 New York US.

Chemical Abstracts, vol. 69, No. 16, Oct. 14, 1968 Columbus, OH, US; abstract No. 067487, p. 6310; col. 2; XP002093429 & Petrov K.A.: "Dialkylphosphinic acids" Khim. Org. Soedin. Fosfora, Akad. NAUK SSSR, Otd. Obshch. Tekh. Khim., 1967, pp. 181–186, SU.

William C. Drinkard: "Some salts of symmetric phosphinic acids" Journal of the American Chemical Society., Bd. 74, Nr. 21, —Nov. 5, 1952 Seiten 5520–5521, XP002093391.

Chemical abstracts vol. 64 abstrac No. 16661 g by Hoffman (6/66).

Houben–Weyl, Methoden der organischen Chemie, vol. XII/1, 4$^{th}$ Edition, 1963, pp. 228ff.

"Phosphinsaure und deren Derivate," Dr. Felcht, vol. E2, 1982, pp. 123 ff.

"Synthesis of DI(n–octyl)phosphinic acid. Influence of the sulfuric acide in the phosphination of 1–octene with sodium hypophosphite,"Martinez, C. Herranz, N. Miralles, & a. Sastre, Afinidad LIII, 466, 1996, pp. 404–406.

CA:107:25119 abs of ES532346 (Jun. 85).

CA:107:176590 abs of Bull Chem Soc Jpn by Ohno 60 (8) pp. 2945–2951 (1987).

CA:107:25119 abs of ES 532346, Jun. 1985.*

\* cited by examiner

*Primary Examiner*—Jean F. Vollano
(74) *Attorney, Agent, or Firm*—Susan S. Jackson; Scott E. Hanf

(57) ABSTRACT

The invention relates to a process for preparing dialkylphosphinic acids and/or alkali metal salts thereof by reacting olefins with alkylphosphonous and/or hypophosphorous acid and/or alkali metal salts thereof, which comprises carrying out the reaction in the presence of a azo free-radical initiator. The invention also relates to the use of the products prepared by the abovementioned process for preparing flame retardants.

15 Claims, No Drawings

PROCESS FOR PREPARING DIALKYLPHOSPHINIC ACIDS

CROSS-REFERENCES TO RELATED APPLICATIONS

This application is a continuation of application Ser. No. 09/198,541, filed Nov. 24, 1998, which is herein incorporated by reference.

FIELD OF THE INVENTION

The invention relates to a process for preparing dialkylphosphinic acids and/or alkali metal salts thereof by reacting olefins with alkylphosphonous and/or hypophosphorous acid and/or alkali metal salts thereof and to the use of the compounds prepared by this process.

BACKGROUND OF THE INVENTION

Owing to the difficulty of their industrial synthesis, dialkylphosphinic acids and their derivatives have been used in industrial areas of application to only a relatively small extent.

Specific secondary phosphines obtained by addition of branched or cyclic olefins to phosphine, after their oxidation to dialkylphosphinic acids, are used as selective extraction media for cobalt/nickel separation.

Mixtures of perfluoroalkylphosphinic acids and perfluoroalkylphosphonic acids are used as specific extraction media. They originate from the reaction of perfluoroalkyl iodides with elemental phosphorus after hydrolysis and subsequent oxidation (DE-A-2 233 941).

To prepare dialkylphosphinic acid derivatives, such as the total herbicide phosphinotricin, a complex synthesis route via the hydrolysis of methyldichlorophosphine to give methylphosphonous acid and subsequent esterification of the abovementioned acid to give a phosphonous ester must be selected, before the second phosphorus-carbon bond can be made under free-radical induction.

The use of dialkylphosphinic acid derivatives as flame retardants for polyesters (poly(ethylene terephthalate) and poly(butylene terephthalate)) is described (EP 0 699 708 A1).

The end products are synthesized in a complex manner using methyldichlorophosphine as organophosphorus starting material, the hydrolysis product methylphosphonous acid and the ester of this acid having to be prepared and isolated as intermediates.

To prepare dialkylphosphinic acids or derivatives thereof, such alkylphosphonous esters can be alkylated by α-olefins at high temperatures under free-radical catalysis conditions. In the case of a reaction of alkylphosphonous acids under the same conditions, only the disproportionation products alkylphosphines and alkylphosphonic acids are obtained, however, whereas under mild conditions no reaction is observed.

U.S. Pat. No. 4,632,741 A1 describes a process for preparing mixtures of salts of alkylphosphonous and dialkylphosphinic acids, by reacting an olefin with a salt of hypophosphorous acid in the presence of a photoinitiator, using UV light.

U.S. Pat. No. 4,590,014 A1 describes a similar process in which the olefin is reacted with the alkali metal salt of hypophosphorous acid in the presence of a free-radical source (peroxide compound). However, the reaction finishes in this case as early as the stage of the alkylphosphonous acid.

According to Martinez et al. [Afinidad 53, 404 (1996)], in the above-described reaction, the yield of dialkylphosphinic acid is increased if said reaction is carried out in the presence of large amounts of sulfuric acid.

However, the above-described processes lead overall to unsatisfactory yields and in virtually all cases, in addition, to a mixture of reaction products, which must be worked up laboriously.

SUMMARY OF THE INVENTION

The object underlying the invention is therefore to provide a process for preparing dialkylphosphinic acids and/or alkali metal salts thereof by reacting olefins with alkylphosphonous and/or hypophosphorous acid and/or alkali metal salts thereof which avoids the abovementioned disadvantages and leads in a short time to high yields of dialkylphosphinic acids and/or alkali metal salts thereof.

This object is achieved by a process of the type described at the outset which comprises carrying out the reaction in the presence of a free-radical initiator.

DESCRIPTION OF THE PREFERRED EMBODIMENTS

Preferably, the olefins are unbranched or branched α-olefins.

Preferably, the α-olefins are ethylene, n-propylene, isopropylene, n-butene, isobutene, n-pentene, isopentene, n-hexene, isohexene, n-octene, isooctene, 1-decene, 1-dodecene, 1-tetradecene, 1-hexadecene, n-eicosene and/or a 2,4,4-trimethylpentene isomeric mixture.

Suitable olefins are compounds of the formula $$\begin{array}{c}R^1\\ \diagdown\end{array}C=C\begin{array}{c}R^3\\ \diagup\end{array}$$
$$\begin{array}{c}R^2\end{array}\diagup\qquad\diagdown\begin{array}{c}R^4\end{array}$$

where $R^1$–$R^4$ can be identical or different and are hydrogen, an alkyl group having from 1 to 18 carbon atoms, phenyl, benzyl or alkyl-substituted aromatics.

Likewise suitable are cycloolefins of the formula $$(CH_2)_n$$

, in particular cyclopentene, cyclohexene, cyclooctene and cyclodecene.

Use can also be made of open-chain dienes of the formula $$\begin{array}{c}R^5\\ \diagdown\end{array}C=C-R^{11}-C=C\begin{array}{c}R^9\\ \diagup\end{array}$$
$$R^6\qquad R^7\qquad R^8\qquad R^{10}$$

where $R^5$–$R^{10}$ are identical or different and are hydrogen or a $C_1$ to $C_6$ alkyl group and $R^{11}$ is $(CH_2)_n$ where n=0 to 6. Preference is given in this case to butadiene, isoprene and 1,5-hexadiene.

Cyclodienes which are preferred are 1,3-cyclopentadiene, dicyclopentadiene and 1,5-cyclooctadiene and also norbornadiene.

Preferably, as olefins, use is made of those having an internal double bond, cyclic or open-chain dienes and/or polyenes having from 4 to 20 carbon atoms.

Preferably, the olefins bear a functional group.

Preferably, the alkylphosphonous acid and/or alkali metal salts thereof are methylphosphonous acid or ethylphosphonous acid and/or alkali metal salts thereof.

Preferably, as free-radical initiators, use is made of azo compounds.

Preferably, the azo compounds are cationic and/or non-cationic azo compounds.

Preferably, as cationic azo compounds, use is made of 2,2'-azobis(2-amidinopropane) dihydrochloride or 2,2'-azobis(N,N'-dimethyleneisobutyramidine) dihydrochloride.

Preferably, as non-cationic azo compounds, use is made of azobis(isobutyronitrile), 4,4'-azobis(4-cyanopentanoic acid) or 2,2'-azobis(2-methylbutyronitrile).

Preferably, as free-radical initiators, use is also made of inorganic peroxide and/or organic peroxide free-radical initiators.

Preferably, as inorganic peroxide free-radical initiators, use is made of hydrogen peroxide, ammonium peroxodisulfate and/or potassium peroxodisulfate.

Preferably, as organic peroxide free-radical initiators, use is made of dibenzoyl peroxide, di-tert-butyl peroxide, and/or peracetic acid.

Preferably, the reaction is carried out in the presence of carboxylic acids.

Particularly preferably, the carboxylic acid is acetic acid.

Preferably, the reaction is carried out at a temperature of from 40 to 130° C.

Particularly preferably, the reaction is carried out at a temperature of from 60 to 100° C.

In particular, the process is preferably carried out at a temperature of from 80 to 5° C.

Preferably, the reaction is carried out in a pressure reactor. This is the case, in particular, if the boiling points of the olefins are below the reaction temperature The present invention also relates in particular to a process in which sodium hypophosphite is reacted with ethylene in the presence of a cationic or non-cationic free-radical initiator or in the presence of a peroxide free-radical initiator to give the sodium salt of diethylphosphinic acid as main product.

The invention also relates to the use of the dialkylphosphinic acids and/or alkali metal salts thereof obtained by the above-described process for preparing flame retardants.

The invention likewise relates to the use of the dialkylphosphinic acids and/or alkali metal salts thereof obtained by the above-described Drocess for preparing flame retardants for thermoplastic polymers.

The invention likewise relates to the use of the dialkylphosphinic acids and/or alkali metal salts thereof obtained by the above-described process for preparing flame retardants for thermoplastic polymers such as poly(ethylene terephthalate), poly(butylene terephthalate), polystyrene or polyamides.

The dialkylphosphinic acids and/or alkali metal salts thereof obtained by the above-described process are also used as additives in polymeric compounds, as extraction media and surfactants.

The invention is described by the examples below.

EXAMPLE 1

100 g (1.25 mol) of methylphosphonous acid were placed in an autoclave together with 5 g (18 mmol, 1.5 mol %) of 2,2'-azobis(2-amidinopropane) dihydrochloride and initially heated to 60° C. with stirring. Ethylene was thereafter introduced into the reactor at a pressure of 20 bar up to saturation. After a reaction time of 17 h at a maximum of 81° C., the reactor was depressurized and cooled. The yield was 135 g.

$^{31}$P-NMR analysis: Methylethylphosphinic acid: 92.4 mol %

| $^{31}$P-NMR analysis: | | |
|---|---|---|
| | Methylethylphosphinic acid: | 92.4 mol % |
| | Methylbutylphosphinic acid: | 6.2 mol % |
| | Methylphophonous acid: | 0.9 mol % |
| | Unknown components: | 0.5 mol % |

EXAMPLE 2

2.2 kg (20.7 mol) of sodium hypophosphite monohydrate were dissolved in 8 kg (7.62 l) of acetic acid and placed in an enamel steel 16 L jacketed pressure reactor. After the reaction mixture was heated to 85° C., ethylene was introduced into the reactor up to saturation via a reducing valve set to 5 bar. The reaction was started under constant stirring by addition of a solution of 56 g (1 mol %) of 2,2'-azobis (2-amidinopropane) dihydrochloride in 250 ml of water and was controlled via the metering rate of the free-radical initiator in such a manner that the reaction temperature in the reactor did not exceed 95° C., with a jacket temperature of 80° C. and constant feed of ethylene at a mean pressure of about 5 bar. The metering time was in total 3 hours. Thereafter, the mixture was allowed to continue to react for a further 3 h at 85° C. The reactor was depressurized, cooled to room temperature and the contents were analyzed.

$^{31}$P-NMR analysis: Diethylphosphinic acid

| $^{31}$P-NMR analysis: | | |
|---|---|---|
| | Diethylphosphinic acid sodium salt: | 87.0 mol % |
| | Ethylbutylphosphinic acid sodium salt: | 11.9 mol % |
| | Ethylphosphonous acid sodium salt: | 0.9 mol % |
| | Hypophosphorous acid sodium salt: | 0.1 mol % |
| | Unknown components: | 0.1 mol % |

The total mass of the contents was 11.7 kg. This corresponds to an ethylene uptake of 1.2 kg (100% of theory).

EXAMLPE 3

2.12 kg (20 mol) of sodium hypophosphite monohydrate were dissolved in 7 kg of acetic acid and introduced into an enamel steel 16 L jacketed pressure reactor. After the reaction mixture was heated to 100° C., ethylene was introduced into the reactor up to saturation via a reducing valve set to 5 bar. In the course of a period of 6 h, a solution of 32.8 g (1 mol %) of azobis(isobutyronitrile) (AIBN) in 500 g of acetic acid was added uniformly with constant stirring at an ethylene pressure of 5 bar and a temperature of 100–105° C. After a post-reaction time of 1 h, depressurization of the reactor and cooling to room temperature, the contents were analyzed.

| $^{31}$P-NMR: | | |
|---|---|---|
| | diethylphosphinic acid sodium salt | 91.3 mol % |
| | butylethylphosphinic acid sodium salt: | 7.7 mol % |
| | ethylphosphonous acid sodium salt: | 0.7 mol % |
| | unknown components: | 0.3 mol % |

The ethylene uptake was 1160 g (100% of theory)

EXAMPLE 4

A mixture of 2.64 kg (20 mol) of a 50% strength aqueous solution of hypophosphorous acid and 7 kg of acetic acid was introduced into an enamel steel 16 L jacketed pressure reactor. After the reaction mixture was heated to 100° C., ethylene was introduced into the reactor up to saturation via a reducing valve set to 5 bar. In the course of a period of 6 h, a solution of 56 g (1 mol %) of 4,4'-azobis(4-cyanopentanoic acid) in 500 g of acetic acid was added uniformly with constant stirring at an ethylene pressure of 5 bar and a temperature of 100–105° C. After a post-reaction time of 1 h, depressurization of the reactor and cooling to room temperature, the contents were analyzed:

| $^{31}$P-NMR: | diethylphosphinic acid: | 90.6 mol % |
|---|---|---|
| | butylethylphosphinic acid: | 8.4 mol % |
| | ethylphosphonous acid: | 0.8 mol % |
| | unknown components: | 0.2 mol % |

The ethylene uptake was 1160 g (100% of theory)

EXAMPLE 5

A solution of 1.5 g (2 mol %) of 2,2'-azobis(2-methylbutyronitrile) in 50 g of acetic acid was added uniformly to a mixture of 42.4 g (0.4 mol) of sodium hypophosphite monohydrate, 134.4 g (1.2 mol) of 1-octene and 1 kg of acetic acid with constant vigorous stirring at 95° C. in the course of a period of 16 h in a 2 L three-neck flask equipped with stirrer, reflux condenser and metering apparatus. After a post-reaction time of 1 h and cooling to room temperature, the contents were analyzed:

| $^{31}$P-NMR: | dioctylphosphinic acid: | 94.1 mol % |
|---|---|---|
| | hexadecyloctylphosphinic acid: | 4.2 mol % |
| | octylphosphonous acid: | 1.1 mol % |
| | unknown components: | 0.6 mol % |

What is claimed is:

1. A process of preparing dialkylphosphinic acids and/or alkali metal salts thereof by reacting olefins with alkylphosphonous and/or hypophosphorous acid and/or alkali metal salts thereof, which comprises carrying out the reaction in the presence of a free radical initiator wherein the free radical initiator is an azo compound.

2. The process as claimed in claim 1, wherein the olefins are unbranched or branched α-olefins.

3. The process as claimed in claim 1, wherein the α-olefins are ethylene, n-propylene, isopropylene, n-butene, isobutene, n-pentene, isopentene, n-hexene, isohexene, n-octene, isooctene, 1-decene, 1-dodecene, 1-tetradecene, 1-hexadecene, n-eicosene and/or a 2,4,4-trimethylpentene isomeric mixture.

4. The process as claimed in claim 1, wherein, as olefins, use is made of those having an internal double bond, cyclic or open-chain dienes and/or polyenes having from 4 to 20 carbon atoms.

5. The process as claimed in claim 1, wherein the olefins bear a functional group.

6. The process as claimed in claim 1, wherein the alkylphosphonous acid and/or alkali metal salts thereof are methylphosphonous acid or ethylphosphonous acid and/or alkali metal salts thereof.

7. The process as claimed in claim 1, wherein the azo compound is cationic or non-cationic.

8. The process as claimed in claim 7, wherein, as cationic azo compounds, use is made of 2,2'-azobis(2-amidinopropane)dihydrochloride or 2,2'-azobis(N,N'-dimethyleneisobutyramidine) dihydrochloride.

9. The process as claimed in claim 7, wherein, as non-cationic azo compounds, use is made of azobis(isobutyronitrile), 4,4'-azobis(4-cyanopentanoic acid) and/or 2,2'-azobis(2-methylbutyronitrile).

10. The process as claimed in claim 1, wherein the reaction is carried out in the presence of carboxylic acids.

11. The process as claimed in claim 10, wherein the carboxylic acid is acetic acid.

12. The process as claimed in claim 1, wherein the reaction is carried out at a temperature of from 40 to 130° C.

13. The process as claimed in claim 1, wherein the reaction is carried out at a temperature of from 60 to 100° C.

14. The process as claimed in claim 1, wherein the reaction is carried out at a temperature of from 80 to 95° C.

15. The process as claimed in claim 1, wherein the reaction is carried out in a pressure reactor.

* * * * *